(12) United States Patent
Jermolovicius et al.

(10) Patent No.: US 7,884,230 B2
(45) Date of Patent: Feb. 8, 2011

(54) PROCESS FOR CHEMICAL RECYCLING OF POST CONSUMPTION POLY(ETHYLENE TEREPHTHALATE) AND APPARATUS FOR CHEMICAL RECYCLING OF POST CONSUMPTION POLYETHYLENE TEREPHTHALATE

(75) Inventors: Luiz Alberto Jermolovicius, Rua Guilherme Bebiano Martins, 93, 04295-020 São Paulo City-SP (BR); Edmilson Renato De Castro, Rua Prof. Heloisa Carneiro, 42-Ap. 14, Jardim Aeroporto, 04630-050 São Paulo City-SP (BR)

(73) Assignees: BRASKEM S.A., Camacari-Ba (BR); Luiz Alberto Jermolovicius, Sao Paulo-SP (BR); Edmilson Renato de Castro, Sao Paulo-SP (BR)

( * ) Notice: Subject to any disclaimer, the term of this patent is extended or adjusted under 35 U.S.C. 154(b) by 0 days.

(21) Appl. No.: 11/660,729

(22) PCT Filed: Aug. 25, 2005

(86) PCT No.: PCT/BR2005/000172

§ 371 (c)(1),
(2), (4) Date: Jun. 22, 2007

(87) PCT Pub. No.: WO2006/021063

PCT Pub. Date: Mar. 2, 2006

(65) Prior Publication Data

US 2008/0097120 A1   Apr. 24, 2008

(30) Foreign Application Priority Data

Aug. 25, 2004   (BR) .................................... 0403740

(51) Int. Cl.
*C07C 63/00*   (2006.01)
(52) U.S. Cl. ........................................ 562/405; 560/78
(58) Field of Classification Search .................... None
See application file for complete search history.

(56) References Cited

U.S. PATENT DOCUMENTS 5,413,681 A * 5/1995 Tustin et al. .................. 203/80

FOREIGN PATENT DOCUMENTS

| DE | 195 34 276 A1 | 3/1997 |
| DE | 19534276 A1 * | 3/1997 |
| WO | WO-95/01953 A1 | 1/1995 |

* cited by examiner

*Primary Examiner*—Sudhakar Katakam
(74) *Attorney, Agent, or Firm*—Birch Stewart Kolasch & Birch, LLP

(57) ABSTRACT

A process for the chemical recycling of post consumption polyethylene terephthalate which includes the steps of performing the depolymerization of polyethylene terephthalate based upon a hydrolysis reaction which causes a rupture in of the ester bonds formed between the polymer precursors of terephthalic acid and ethylene glycol at the time of polymerization to recover terephthalic acid and ethylene glycol. The advantages of the present process are the working conditions at low to moderate pressure, at temperatures of 215 to 450° C., allowing the process to reach the energy level required to achieve the desired polyethylene terephthalate hydrolysis and simultaneously promoting the separation and purification of the terephthalic acid and ethylene glycol formed in this hydrolysis reaction.

11 Claims, 7 Drawing Sheets

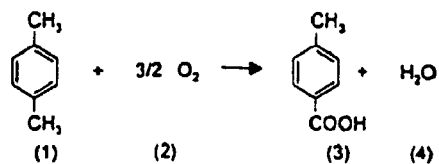
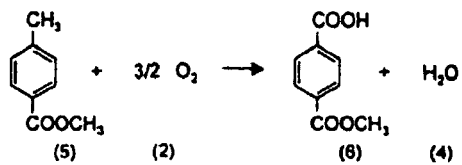
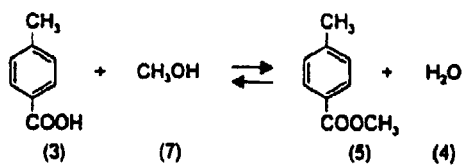
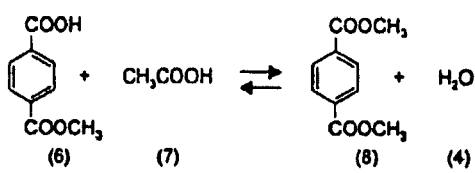
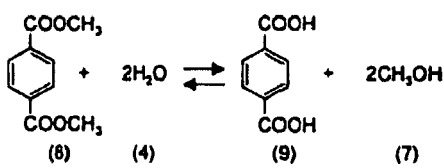
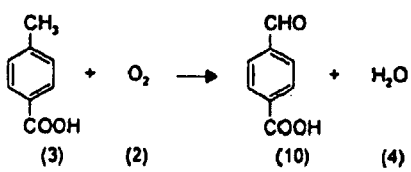
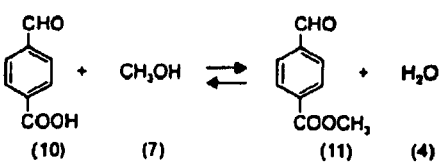
*FIG. 1*

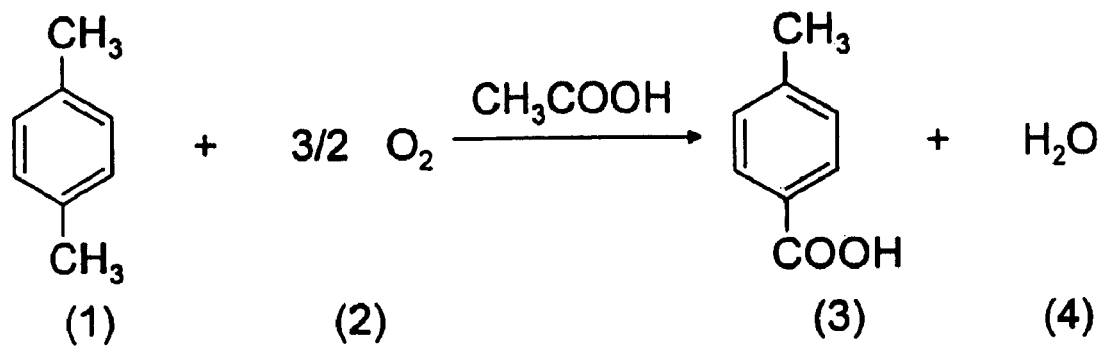
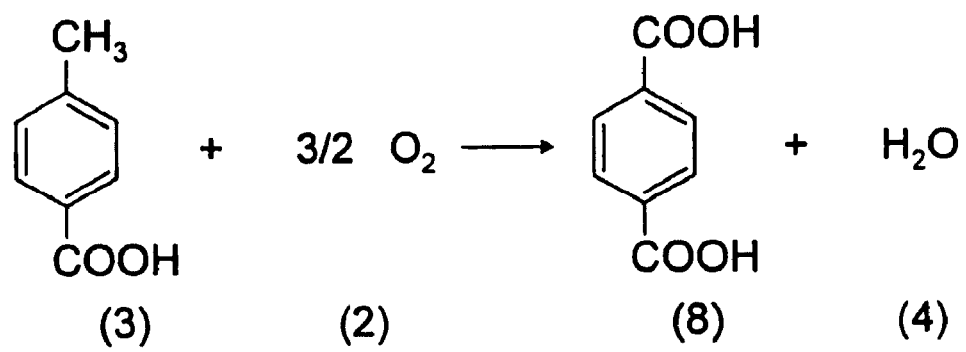
FIG. 2

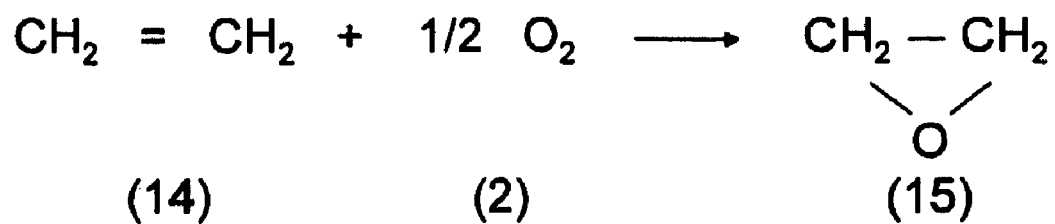
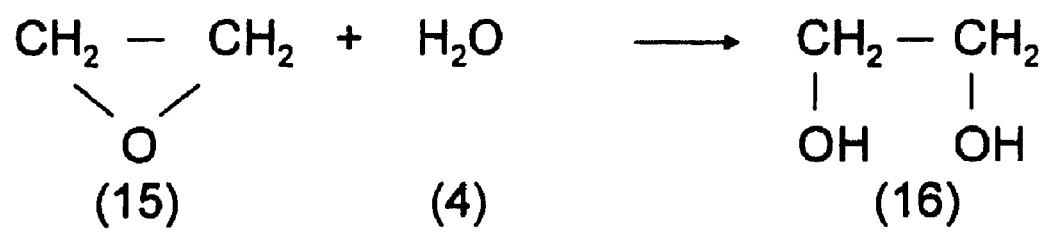
*FIG. 4*

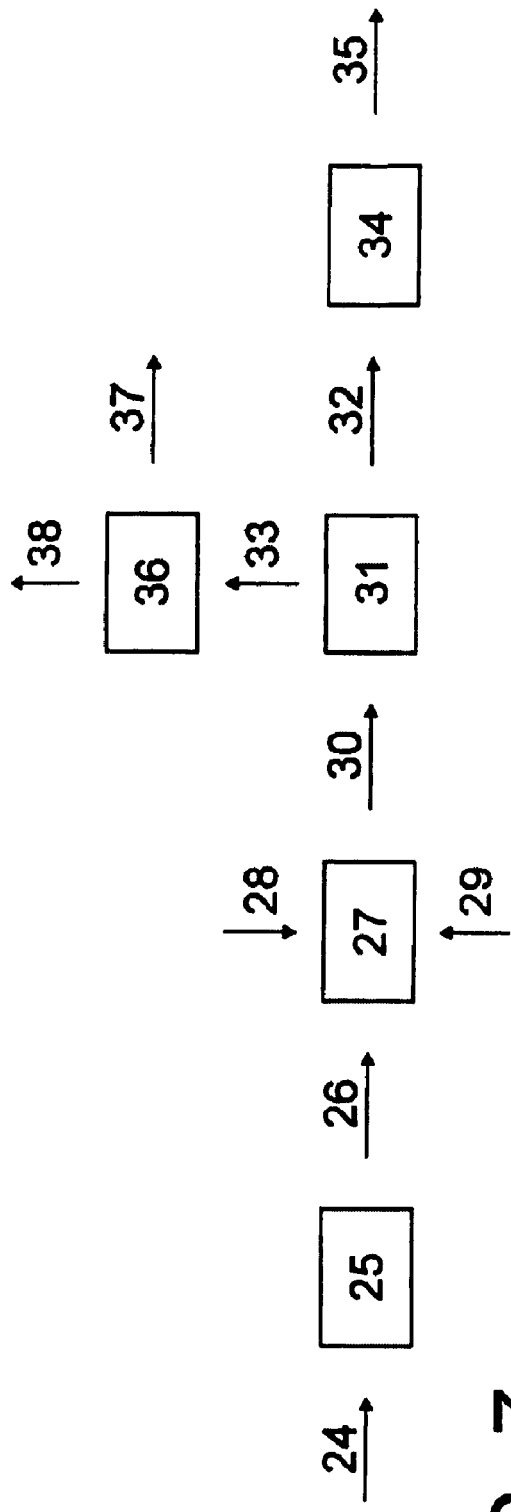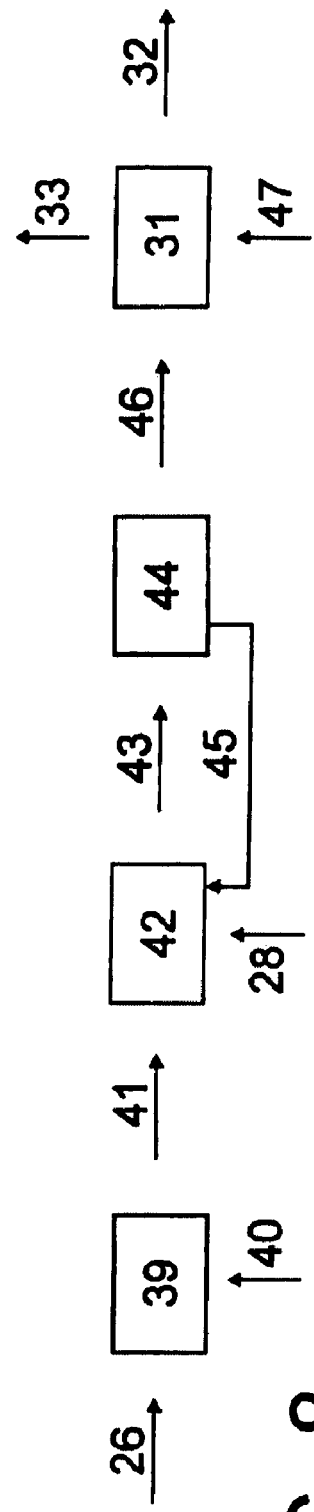
FIG. 7
FIG. 8

PROCESS FOR CHEMICAL RECYCLING OF POST CONSUMPTION POLY(ETHYLENE TEREPHTHALATE) AND APPARATUS FOR CHEMICAL RECYCLING OF POST CONSUMPTION POLYETHYLENE TEREPHTHALATE

TECHNICAL FIELD

The present invention is directed to a process for the chemical recycling of post consumption polyethylene terephthalate and the equipment used to perform this recycling.

BACKGROUND ART

The chemical recycling of polyethylene terephthalate, PET, post consumption, consists of a set of procedures to promote its depolymerization and regenerate its raw materials: terephthalic acid and ethylene glycol. Part of the procedures is mechanical, such as the collection of PET pieces, such as beverage bottles and discarded artoc;es in general, and the transportation, compaction, baling, comminution, elimination of undesired polymers, washing, drying and other complementary processes performed to aggregate to produce so called "solid residue".

Another part of these procedures includes the depolymerization of PET into terephthalic acid and ethylene glycol, and the subsequent purification of these products. Each one of the procedures utilized herein has its appropriate equipment for its performance.

Distinct processes for the production of terephthalic acid are in the state of the art. There are also the process for producing the dimethyl terephthalate, instead of terephthalic acid, due to the difficulty of purification of the terephthalic acid.

In the polymerization for the production of PET, dimethyl terephthalate provides worst polymerization conditions than terephthalic acid, such as for example a lower polymerization rate, a higher consumption of ethylene glycol and formation of residual methanol.

Therefore, the manufacturing processes of said diester lost preference and the route more employed for the manufacturing of terephthalic acid consists in the catalytic oxidation in liquid phase of p-xylene to terephthalic acid.

The processes are based on the formation of a dimethyl ester of terephthalic acid, where a catalytic oxidation is processed in liquid phase of p-xylene 1 and methyl p-methyltoluate 5, with air oxygen 2, producing p-toluic acid 3 and methyl mono ester of terephthalic acid 6 and water 4 as co-product.

This mixture is esterified with methanol 7, producing the methyl p-methyltoluate 5 and dimethyl terephthalate 8, as presented in FIG. 1.

After the esters are separated by distillation, the dimethyl terephthalate 8 can be hydrolyzed into terephthalate acid 9.

The p-carboxyaldehyde 10, formed as an intermediate in the p-xylene 1 oxidation with oxygen 2, is also esterified with methanol 7 into methyl p-carboxytoluate 11 and this ester, by its turn, is hydrolyzed with water 4 regenerating the p-carboxyaldehyde 10 as is also presented in FIG. 1.

The direct oxidation into terephthalic acid consists in a chemical process of structure change of the raw material, p-xylene, which is an aromatic hydrocarbon, to the structure of a dicarboxylacid, in this case terephthalic acid.

This processing is performed in continuous chemical reactors, where the following reactions presented in FIG. 2 occur, where the p-xylene is oxidized by air oxygen 2, in the presence of acetic acid as solvent and cobalt acetate, sodium bromide, carbon tetrabromide as catalyst/co-catalyst, at 175-230° C. and 15-35 bar, forming the p-toluic acid 3 and this, by its turn, is oxidized to terephthalic acid 4.

Actually, the main reactions are a simplification of the complete mechanism presented in FIG. 3, where the intermediate steps of p-xylene 1 oxidation into p-methylbenzyl hydroperoxide 12, from this to p-tolualdehyde 13, then to p-toluic acid 3, then to p-carboxyaldehyde 10 and finally to terephthalic acid 8. As the reactions show, it is a process occurring in successive oxidation steps. If the intermediate oxidation reactions are not taken to its own complementation, at the end of the process, intermediate products such as process undesired by-products will remain. The control over these serial reactions will determine the degree of contamination of the terephthalic acid produced and define its impurities.

The intermediate substances accompanying the terephthalic acid cause problems to the polymerization process in PET manufacturing, for example, the p-methylbenzoic acid 3 delays the polymerization and leads to the obtainment of a low-molecular weight polymer. Another example is the p-carboxyaldehyde 10 that causes the coloration in the terephthalic acid.

The main purification step of the raw terephthalic acid is its hydrogenation, in aqueous suspension and in the presence of a palladium coal-supported catalyst, at 250° C., when the p-carboxyaldehyde 10 is reduced to toluic acid 3. A subsequent purification is the terephthalic acid 8 crystallization. And the final purification consists in a sublimation of the re-crystallized terephthalic acid. Only with this purification sequence is it possible to reach the purity degree required for terephthalic acid to be appropriate to the production of PET. All this work is due to the formation of p-carboxyaldehyde, which is admitted, at most, in a level of 25-50 ppm in polymerization grade terephthalic acid.

The sublimation is a product based on the steam pressure value of the solid terephthalic acid and it is a single, slow, operation, requiring large volume equipment due to the low mass and heat exchange rate during sublimation. There is also an aggravating point: according to the intensity of heating at sublimation, the terephthalic acid formed transforms into terephthalic anhydride.

In order to avoid that this new impurity follows the product intended to polymerization, the sublimated terephthalic acid is treated with water steam and, later, subjected to drying.

According to the state of the art, a manufacturing route of ethylene glycol 16, main diol used in the PET manufacturing, is the water 4 hydrolysis of the ethylene oxide 15, manufactured from the ethylene 14 by catalytic oxidation with air oxygen 4, as summarized in FIG. 4.

According to the state of the technique, the PET recycling can be classified into two large universes: mechanical recycling (where the PET chemical structure is not altered) and chemical recycling (where the original PET structure goes through a molecular change).

The mechanical recycling presents successive physical operations viewing to aggregate value to the solid residues constituted by PET, conducting the different articles manufactured in PET to the shape of flakes and granulate. The PET flakes are particles with millimeter dimensions of PET, obtained by communition of PET residues, and that might be marketed, within the recycling chain, for the production of granulates. The granulates are PET particles obtained by the melting of flakes and, subsequent melted material granulation, and constitute the basic final product of the mechanical recycling line of post consumption PET.

The steps of the transformation of PET articles into flakes and/or granulates comprise the following sequence of operations: a) collection of post consumption PET articles, i.e., selective collection of PET wastes from urban garbage; b) classification, done in mats that transport the acquired material while operators select the elements that are not PET and remove them from the mat; c) milling and washing, which is done in humid mills, where PET is comminuted; d) rinsing, done in two transporting threads, where the washing water is separated; d) separation and decontamination, which is done in a tank an endless thread to remove materials different from PET; f) pre-drying, which is made in a vertical centrifuge, where the water accompanying the PET flakes is separated; g) drying and dust elimination, which is done in a continuous hot-air electric drier, where the flake is dried and the dust formed is dragged in the air; h) particles classification, which is done in a vibrating sieve, where the PET flakes are separated according to their granulometry; i) bagging, which is done by a bagger.

A later treatment that aggregates value to recycled PET is its granulation by controlled heating, when the flakes are transformed into granules.

The chemical recycling can be understood at two levels: "recondensation" level (where the PET granulate is treated in order to increase its mean molecular weight) and the depolymerization level (where the PET molecule is totally destroyed, yielding terephthalic acid and ethylene glycol).

The recondensation views to correct the mean molecular weight of the recycled PET. During the conformation processes of the virgin PET and mechanical recycling processes of post consumption PET, the polymer molecules suffer heating and mechanical stresses causing a certain degree of breaking of these macromolecules, resulting in a decrease of mean molecular weight.

The recondensation consists in a chemical process where the recycled polymer is subjected to high temperatures and high vacuum, in the presence of catalysts, forcing the broken molecules to react among themselves and increase the mean molecular weight (U.S. Pat. No. 6,436,322, U.S. Pat. No. 4,657,988, CA 1277081). The inconveniency of this process is that the molecular weight distribution profile is not remade, but only the mean molecular weight is increased to the levels of the original polymers.

The depolymerization is based in the hydrolysis reaction, which is a typical reaction of esters, PET is a polyester, i.e., a macromolecule constituted by the repetition of interlinked monomers by the chemical bond between the molecular structures of the terephthalic acid and ethylene glycol.

FIG. 5 shows the formation of the ester binding in the PET 17 polymerization. This chemical bond between an acid (in this case, terephthalic acid) and an alcohol (in this case, ethylene glycol) is called ester binding and the product constitutes an ester (in this case, PET).

The esters are susceptible to a series of reactions, among them with water 4, organic acids 18, alkalis such as soda 20 and alcohols 22 reactions. In these four reactions, the ester binding is broken and in the case of PET 17, the following are respectively formed: terephthalic acid 10 and ethylene glycol 16—this reaction is called hydrolysis; terephthalic acid 10 and ester of the acid employed with ethylene glycol 19—this reaction is called acidolysis; sodium terephthalate 21 and ethylene glycol 16—this reaction is called saponification; terephthalate 23 of alcohol 22 used and ethylene glycol 16—this reaction is called alcoholysis. In FIG. 6 a table is presented showing these reactions.

From this point of view of the chemical reactions, the acidolysis, saponification and alcoholysis are particular cases of the hydrolysis reaction. The hydrolysis itself would be the ester reaction with water, both without catalysis or with acid catalysis (acid hydrolysis) or alkaline (alkaline) hydrolysis). Note that the difference between acidolysis or saponification and acid or alkaline hydrolysis is the amount of acid or alkali used. In the first two cases, the amounts are the stoichiometrically required for a complete reaction of the ester. In the second case, the acid and alkali enter only in catalytic proportions (very small compared to the amount of ester) and are intended to promote the reaction mechanisms faster than the ones of a hydrolysis with no catalysis.

Some patented processes for the performance of this hydrolysis reaction without catalyst (U.S. Pat. No. 3,120, 561), acid hydrolysis (U.S. Pat. No. 3,355,175), alkaline hydrolysis and saponification (WO 95/10499, U.S. Pat. No. 6,031,128, U.S. Pat. No. 4,193,896), acidolysis (WO 03033581, U.S. Pat. No. 5,948,934) and alcoholysis (U.S. Pat. No. 5,559,159) are in the state of the art. Such processes, based on the hydrolysis process, according to the state of the art, generically consist in the PET comminution, in the polymer hydrolysis and in the purification of the terephthalic acid obtained. This purification consists in a precipitation of the terephthalic acid and subsequent purification by crystallization. The terephthalic acid produced by this way still needs the sublimation purification in order to be classified with a polymerization grade, due to the presence of low molecular weight oligomers formed as intermediates during the hydrolysis reactions.

DISCLOSURE OF THE INVENTION

The present invention is directed to a process of chemical recycling of post consumption polyEthylene Terephthalate and the apparatus required to perform the chemical recycling of the post consumption polyEthylene Terephthalate, the proposed process containing the chemical recycling of PET in order to promote PET hydrolysis, that yields terephthalic acid and ethylene glycol and/or another glycol that has been used in the PET formulation, and, also, at the hydrolysis moment, to promote the separation of the terephthalic acid from the reagent mixture for its purification.

Due to the state of the art, the applicants started studies viewing the development of "Process for Chemical Recycling of Post Consumption Poly(Ethylene Glycol) and Equipment to Perform Chemical Recycling of Post Consumption Poly (Ethylene Terephthalate)" performing the depolymerization of the PET conducted in conditions that allow to reach the energy level required for the desired PET hydrolysis, and simultaneously promote the separation and purification of the terephthalic acid and ethylene glycol and/or another glycol present in the PET formulation formed in this hydrolysis reaction. The advantage, from the point of view of chemical process, is the elimination of the occurrence of contaminants such as p-carboxyaldehyde, p-toluic acid and oligomers, and also allow the contiguous purification of the terephthalic acid produced. The present invention utilizes a smaller number of operation equipment than the state of the art while achieving the same purity level in its products as in conventional processes. Allied to this aspect, is the fact that the process is operated at room or low pressure, while the processes of the state of the art tend to reach high pressures. Its advantage is due to the change of concept to perform the hydrolysis reaction. Instead of using a reagent, as an acid or alkali to catalyze the reaction, the water itself is used to promote the hydrolysis, resulting in a short time of permanence of the reactive products in the reaction conditions, and moderate, overall operation conditions in the chemical reactor, although sufficient to meet the thermodynamic needs of the hydrolysis reaction in question. The advantage, from the ecologic point of view is the effective elimination of PET, that other forms of PET mechanical recycling would not allow to perform, as the only change its form, allowing them to accumulate in the biosphere.

These advantages on the state of the art are reached by the Process for Chemical Recycling of Post Consumption polyEthylene terephthalate and Equipment to Perform the Chemical Recycling of Post Consumption polyEthylene terephthalate in a continuous mechanical-electric equipment, provided with a solid polymer moving system as flakes or granulates, that are taken across a heated chamber by the means of thermal change with appropriate thermal fluids, by means of electric resistances or by methods based on the electro-resistive heating or by electromagnetic radiations such as microwaves, ultrasound or radio frequency.

In this chamber, the processing polymer has its state changed, melting and changing to a viscous liquid at the melting temperature between 220 and 280° C. The viscosity is due to the high molecular weight of PET. The temperature and heat flow in this chamber are enough to promote the melting, keep it melted, but without pyrolysis.

In a contiguous chamber, analogue to the previous one and operated in more drastic conditions, the melted polymer has its temperature increased to temperatures that propitiate a high molecular agitation energy, such as those obtained in the range of 300 to 450° C., at room pressure.

In the same chamber, the breaking of the polymeric structure, in its weaker points, i.e., in the ester bonds, is promoted by the introduction of fluid both as liquid and steam, allowing the hydrolysis reaction of the ester bonds, in PET case.

This liquid can be any polar compound, such as alcohols, carboxylacids or even water. It can be stimulated by the presence of an appropriate catalyst such as inorganic acids, alkalis, amines. As the structure is broken, the chemical structures of its precursors are formed, i.e., its raw materials—terephthalic acid and ethylene glycol.

A creeping fluid current, which may be a gas current, such as nitrogen or carbonic gas, as well as water steam or excessive hydrolytic agent, is used. This creeping current removes the products formed from the high energy density zone, directing them to a chamber where the temperature is increased, about 400 to 500° C., also under room pressure, where, due to its appropriate dimensions the fractioning of the product is obtained in two currents: a) liquid phase containing the non totally reacted material and it is recycled at the fresh polymer feeding, and discarded in part to avoid high concentration of wastes; and b) creeping fluid disperse phase, where a terephthalic acid suspension is seen. This gas phase with suspension is dragged, with the water steam current to avoid the formation of terephthalic anhydride, to a condenser-type separator assembled to a cyclone, to separate the solid and condensed phase from the residual gas phase. The solid, the terephthalic acid, is filtered and washed, being submitted to a final drying. The aqueous phase is used to recover the ethylene glycol through a fractioned distillation.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein:

FIG. 1—represents the chemical equations of the reactions occurring in the manufacturing process of the terephthalic acid through its methyl ester;

FIG. 2—represents the chemical equations of the main reactions occurring in the oxidation process of p-xylene to terephthalic acid;

FIG. 4—represents the chemical equations of the reactions occurring in the manufacturing process of ethylene glycol;

FIG. 7—is the blocks diagram showing the steps of the process innovated herein; and FIG. 8—is a scheme drawing of the structure of the equipment innovated herein, where the process mentioned is performed.

DETAILED DESCRIPTION OF THE INVENTION

Figure 3:
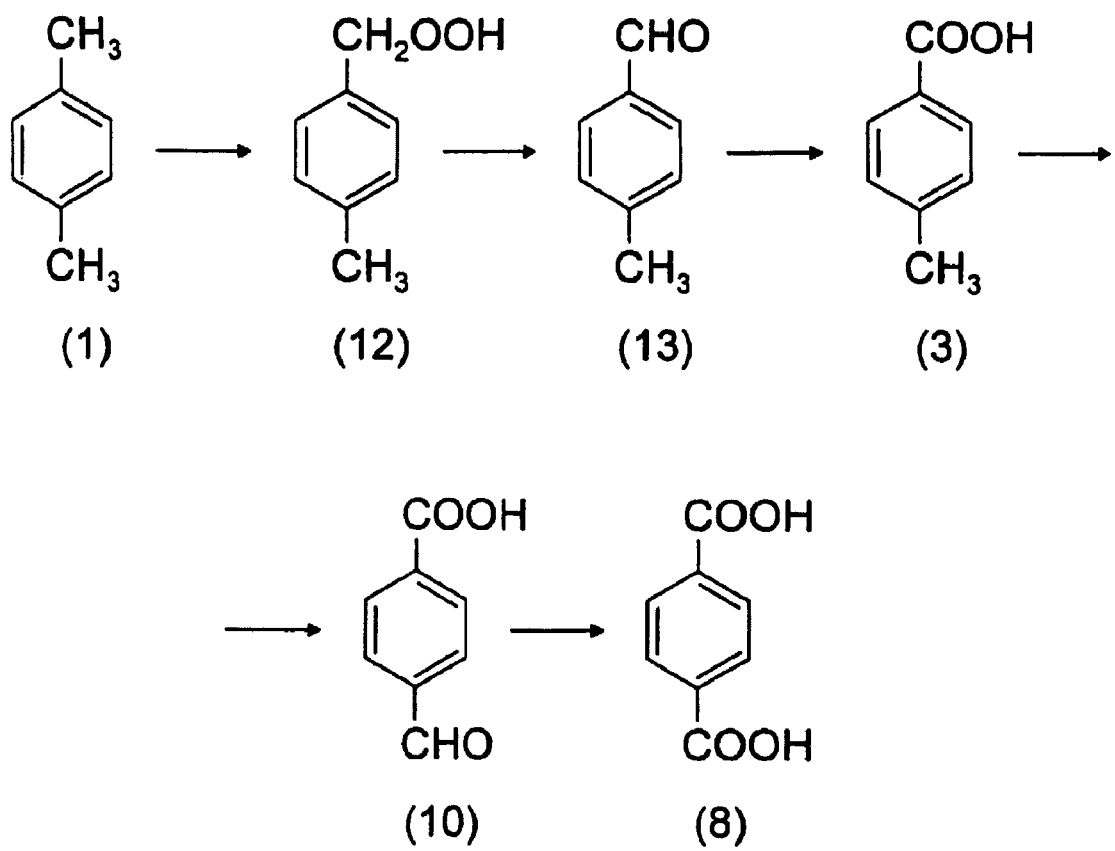
FIG. 3—represents the complete chemical equations of the reactions occurring in the oxidation process of p-xylene to terephthalic acid.
Figure 5:
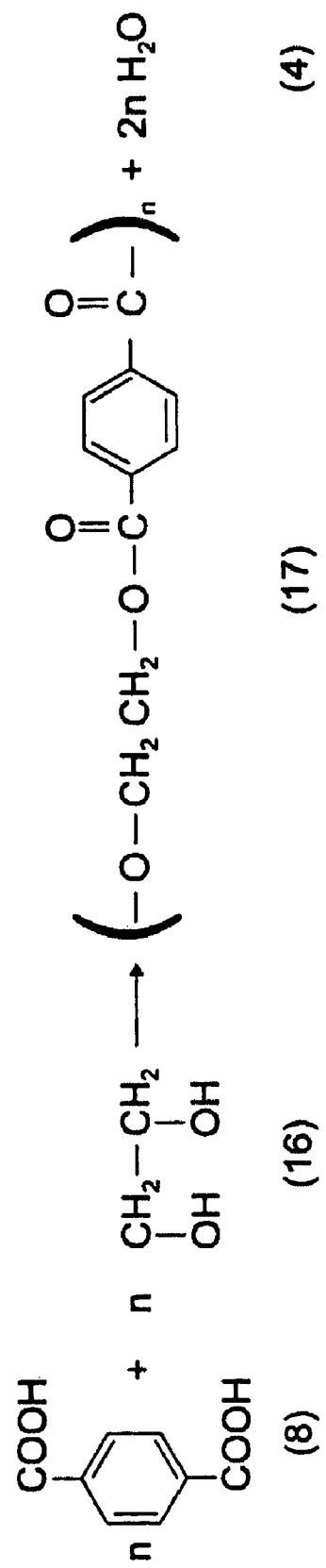
FIG. 5—represents the chemical equations of the reactions occurring in the manufacturing process of PET.
Figure 6:
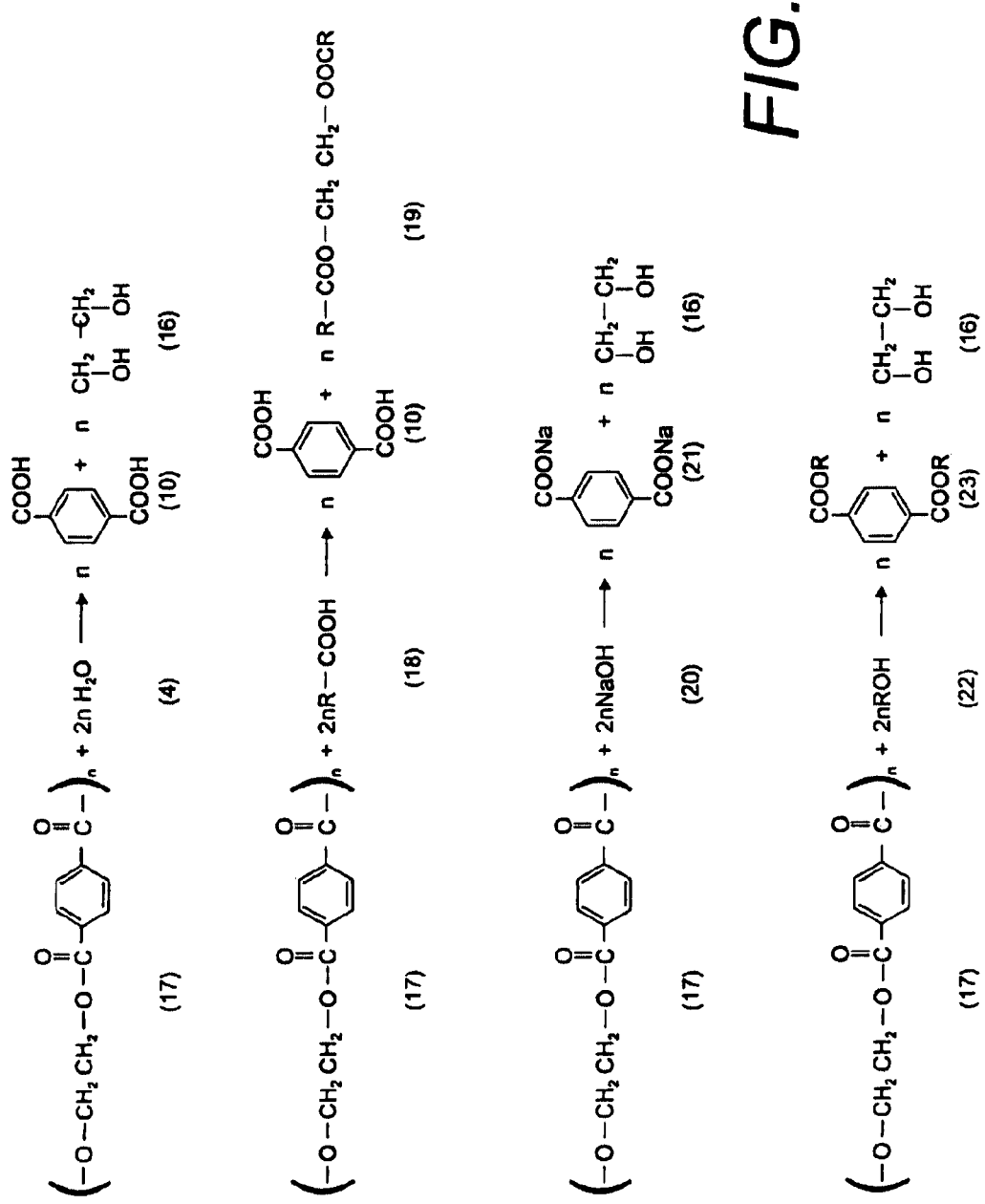
FIG. 6—represents the possible ways to promote PET depolymerization.

The subject of the present invention is constituted by the following steps, with reference to FIG. 7: feeding of post consumption PET articles and wastes 24 to a preparation area 25 of post consumption PET loading, where it is washed and comminuted to flakes of different sizes ranging from 2 mm×7 mm to 7 mm×10 mm, preferably between 3 mm×6 mm.

The flake PET 26 is continuously fed to the depolymerizer 27, simultaneously with the feeding of a depolymerization agent, such as caustic soda, caustic potash, soda ash or another appropriate alkali, sulphuric acid, phosphoric acid, methanesulphonic acid, p-toluene sulphonic acid or another appropriate acid, water steam and/or liquid water, as a solution of the above mentioned depolymerizing agents or as a pure product 28 as well as a creeping fluid current such as nitrogen, carbonic gas or another gas or even water steam 29.

The depolymerization product 30 constituted by a mass of terephthalic acid, ethylene glycol and waste water is fed into a solids separator 31, where the solid phase of terephthalic acid 32 and the liquid-phase of ethylene glycol and water 33 are separated.

The terephthalic acid 32 obtained thereby can have its purity degree increased via purification treatment 34, common in the petrochemical industry, in order to obtain the polymerization grade terephthalic acid, also called PTA (pure terephthalic acid) 35.

The liquid fraction 33 constituted by water, ethylene glycols and other glycols eventually present in the formulation of processed PET is fed into a glycols purifier 36 that can be a conventional distillation column to separate water 37 from ethylene glycol 38.

The equipment shown schematically in FIG. 8 comprises a chamber 39, where the flakes or granules of PET 26 are conveyed through a mechanism such as a thread transporter, a mechanical stirrer or any other solids propeller.

Simultaneously to this transportation, PET is heated through an energy supply 40 by electric resistance, heat exchangers or electromagnetic wave radiators, such as ultrasound or microwaves of 915 MHz to 10 GHz. This energy supply 40 must be such so as not to reach the decomposition level by PET pyrolysis.

The flake PET 26 after this treatment has its amount of energy increased in order to become inclined to the reaction with a depolymerization agent 28. This agent 28 and this PET properly activated 41 in the above mentioned chamber 39 are mixed in another chamber 42, providing a close contact for the time required, from 1 minute to 16 minutes, eventually lower than 1 minute, due to the energy level reached, that might be seen by the processing temperature between 215 and 450° C., preferably between 250 and 350° C., in order to promote the PET depolymerization reaction.

The effluent 43, still at the temperature when it left the chamber 42 is submitted to a phase separation in an appropriate enlarging 44, such as a decanting vase or an obstacle to the fluid flow 43.

This section 44 is operated at a convenient temperature for the separation and recycling, at the previous step 42, of the liquid phase 45 of non-reacted PET.

The non-liquid product separated on 44 is constituted by terephthalic acid, ethylene glycol, other eventual glycols and waste water, and is sent to chamber 31. In the chamber 31, constituting in an enlargement of the chamber 44, the material is quickly cooled by water injection 47 as a jet or shower, obtaining a terephthalic acid decantation product 32 and ethylene glycol or another glycols solution 33.

Terephthalic acid manufacturing experiences were performed, using the decreased scale equipment, processing a load of flake PET from a mechanical process of recycling, at a flow rate of 1.6 to 2.5 g/min, obtaining a terephthalic acid yielding, on the stoichiometric and by pass, of 64%.

The invention claimed is:

1. A continuous process for the chemical treatment of polyethylene terephthalate in the form of flakes granules or scraps to recover terephthalic acid and ethylene glycol which comprises melting the polyethylene terephthalate at a temperature of 220 to 280° C. to form a molten liquid, increasing the temperature of the molten, liquid polyethylene terephthalate to a temperature of 300 to 450° C. at ambient pressure, and depolymerizing the molten liquid polyethylene terephthalate by introducing water to the molten, liquid polyethylene terephthalate, said water being converted to overheated steam, the overheated steam expanding to provide an intimate mixture thereof with the molten polyethylene terephthalate, thereby hydrolyzing the molten polyethylene terephthalate with simultaneous sublimation, whereby terephthalic acid and ethylene glycol are separated from unreacted molten liquid polyethylene terephthalate.

2. The continuous process of claim 1, wherein the hydrolysis of the molten polyethylene terephthalate produces, as a vapor phase, a mixture of terephthalic acid vapor, ethylene glycol vapor and steam, and said vapor phase is separated from a remaining liquid phase of unreacted molten polyethylene terephthalate by said sublimation.

3. The continuous process of claim 1, wherein during hydrolysis, the temperature of the unreacted molten liquid polyethylene terephthalate is increased during hydrolysis to 400 to 450° C.

4. The continuous process of claim 2, wherein the liquid phase is partially discarded and the non-discarded fraction is recycled for further hydrolysis.

5. The continuous process of claim 1, conducted at a pressure of from ambient pressure to 10 atm.

6. The continuous process of claim 1, wherein the hydrolysis is facilitated by the addition of caustic soda, caustic potash, soda ash or an alkali.

7. The continuous process of claim 2, wherein heating is applied to maintain a melted condition of the polyethylene terephthalate as the temperature increases from 215 to 450° C. but said temperature is controlled to prevent pyrolysis of the polyethylene terephthalate, said heating being conducted for a period of 1 to 16 minutes.

8. The continuous process of claim 1, wherein depolymerization is facilitated by the addition of an organic acid or an inorganic acid.

9. The continuous process of claim 1, wherein mineral oils or synthetic oils are added to facilitate polyethylene terephthalate depolymerization.

10. The continuous process of claim 1, wherein nitrogen or carbonic acid are added to the process during the depolymerization step.

11. The continuous process of claim 1, wherein microwave radiation or radio-frequency energy is used to supply the heat for polyethylene terephthalate depolymerization.

* * * * *